United States Patent
Eby et al.

(10) Patent No.: US 10,398,876 B2
(45) Date of Patent: Sep. 3, 2019

(54) SYSTEM AND METHODS FOR LEADLESS PACING USING NEGATIVE PRESSURE

(71) Applicant: Pacesetter, Inc., Sunnyvale, CA (US)

(72) Inventors: Thomas B. Eby, Mountain View, CA (US); Arundhati Kabe, Sunnyvale, CA (US); Paul Paspa, Los Gatos, CA (US)

(73) Assignee: PACESETTER, INC., Sylmar, CA (US)

( * ) Notice: Subject to any disclaimer, the term of this patent is extended or adjusted under 35 U.S.C. 154(b) by 79 days.

(21) Appl. No.: 15/497,890

(22) Filed: Apr. 26, 2017

(65) Prior Publication Data
US 2018/0310949 A1 Nov. 1, 2018

(51) Int. Cl.
| | | |
|---|---|---|
| *A61B 17/30* | (2006.01) | |
| *A61M 25/00* | (2006.01) | |
| *A61N 1/375* | (2006.01) | |
| *A61N 1/372* | (2006.01) | |
| *A61N 1/362* | (2006.01) | |
| *A61N 1/05* | (2006.01) | |

(52) U.S. Cl.
CPC ......... *A61M 25/0082* (2013.01); *A61N 1/372* (2013.01); *A61N 1/3756* (2013.01); *A61B 2017/306* (2013.01); *A61N 1/0573* (2013.01); *A61N 1/362* (2013.01)

(58) Field of Classification Search
CPC .... A61N 1/3756; A61N 1/0573; A61N 1/362; A61N 1/372; A61B 17/30; A61B 17/3468; A61B 2017/00367; A61B 2017/00539; A61B 2017/00544; A61B 2017/306; A61M 25/0082
See application file for complete search history.

(56) References Cited

U.S. PATENT DOCUMENTS

| | | |
|---|---|---|
| 9,511,219 B1 | 12/2016 | Datta |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088400 A1 | 4/2007 | Jacobson |
| 2007/0088405 A1 | 4/2007 | Jacobson |
| 2007/0088408 A1 | 4/2007 | Jacobson |
| 2007/0088418 A1 | 4/2007 | Jacobson |
| 2011/0270339 A1 | 11/2011 | Murray, III et al. |
| 2018/0178006 A1* | 6/2018 | Soltis .................... A61N 1/372 |

FOREIGN PATENT DOCUMENTS

WO 2007/047681 A2 4/2007

* cited by examiner

*Primary Examiner* — George J Ulsh
(74) *Attorney, Agent, or Firm* — Theresa Raymer

(57) ABSTRACT

Disclosed herein is a system for delivering a leadless pacemaker having a housing with a proximal end. The system includes a guide catheter. The guide catheter includes a catheter shaft and a negative pressure attachment feature. The catheter shaft includes a distal end and a proximal end opposite the distal end. The negative pressure attachment feature is located at the distal end of the catheter shaft and configured to selectively negative pressure adhere with the housing of the leadless pacemaker.

4 Claims, 11 Drawing Sheets

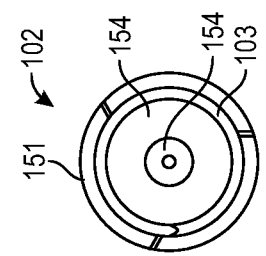
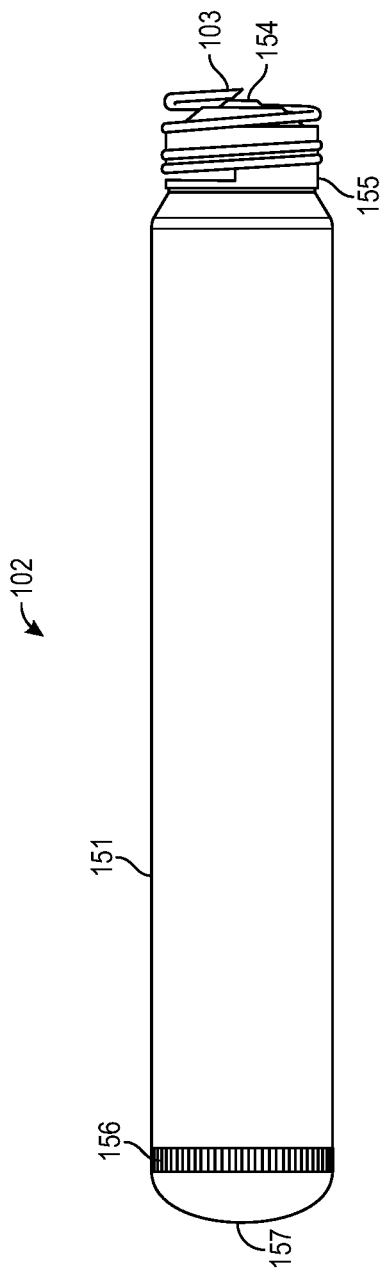

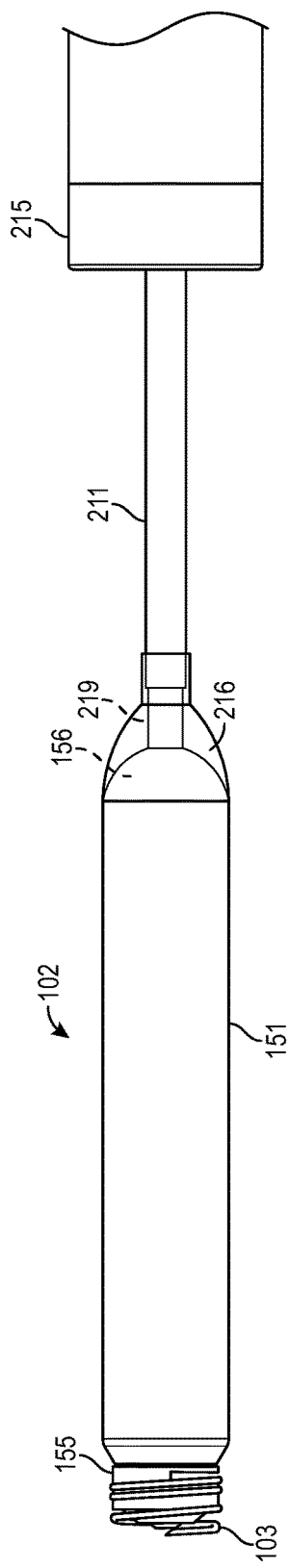
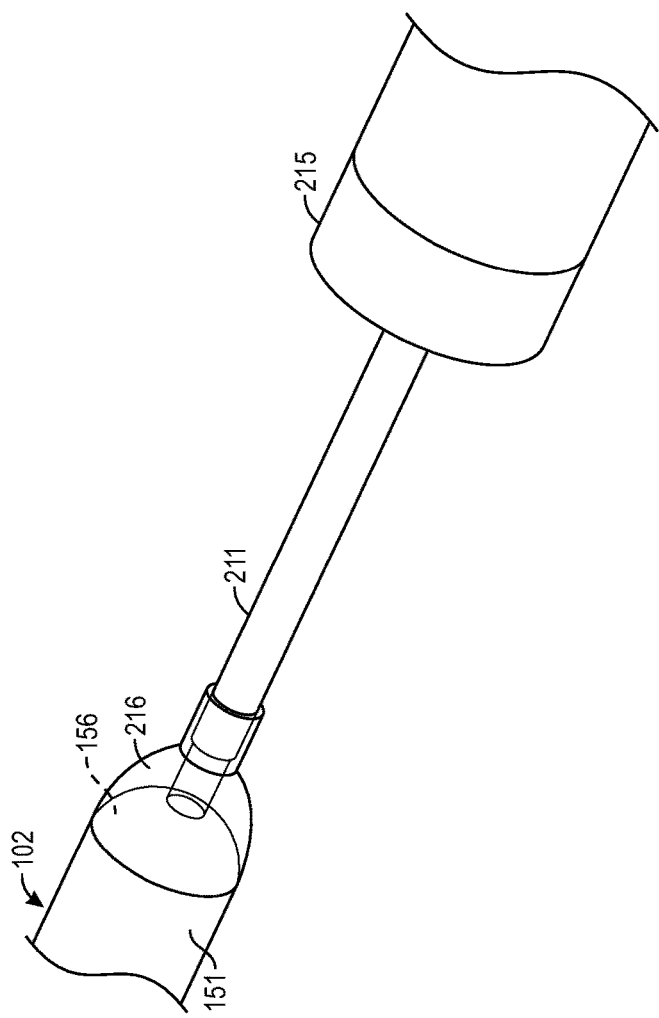
FIG. 3
FIG. 4

SYSTEM AND METHODS FOR LEADLESS PACING USING NEGATIVE PRESSURE

INCORPORATION BY REFERENCE

All publications and patent applications mentioned in this specification are herein incorporated by reference to the same extent as if each individual publication or patent application was specifically and individually indicated to be incorporated by reference.

FIELD

The present disclosure relates to leadless cardiac pacemakers and related delivery systems and methods. More specifically, the present disclosure relates to catheter-based delivery systems and methods for delivering leadless pacemakers.

BACKGROUND

Cardiac pacing by an artificial pacemaker provides an electrical stimulation of the heart when its own natural pacemaker and/or conduction system fails to provide synchronized atrial and ventricular contractions at rates and intervals sufficient for a patient's health. Such antibradycardial pacing provides relief from symptoms and even life support for hundreds of thousands of patients. Cardiac pacing may also provide electrical overdrive stimulation to suppress or convert tachyarrhythmias, again supplying relief from symptoms and preventing or terminating arrhythmias that could lead to sudden cardiac death.

Cardiac pacing by currently available or conventional pacemakers is usually performed by a pulse generator implanted subcutaneously or sub-muscularly in or near a patient's pectoral region. Pulse generator parameters are usually interrogated and modified by a programming device outside the body, via a loosely-coupled transformer with one inductance within the body and another outside, or via electromagnetic radiation with one antenna within the body and another outside. The generator usually connects to the proximal end of one or more implanted leads, the distal end of which contains one or more electrodes for positioning adjacent to the inside or outside wall of a cardiac chamber. The leads have an insulated electrical conductor or conductors for connecting the pulse generator to electrodes in the heart. Such electrode leads typically have lengths of 50 to 70 centimeters.

Although more than one hundred thousand conventional cardiac pacing systems are implanted annually, various well-known difficulties exist, of which a few will be cited. For example, a pulse generator, when located subcutaneously, presents a bulge in the skin that patients can find unsightly, unpleasant, or irritating, and which patients can subconsciously or obsessively manipulate or "twiddle". Even without persistent manipulation, subcutaneous pulse generators can exhibit erosion, extrusion, infection, and disconnection, insulation damage, or conductor breakage at the wire leads. Although sub-muscular or abdominal placement can address some concerns, such placement involves a more difficult surgical procedure for implantation and adjustment, which can prolong patient recovery.

A conventional pulse generator, whether pectoral or abdominal, has an interface for connection to and disconnection from the electrode leads that carry signals to and from the heart. Usually at least one male connector molding has at least one terminal pin at the proximal end of the electrode lead. The male connector mates with a corresponding female connector molding and terminal block within the connector molding at the pulse generator. Usually a setscrew is threaded in at least one terminal block per electrode lead to secure the connection electrically and mechanically. One or more O-rings usually are also supplied to help maintain electrical isolation between the connector moldings. A setscrew cap or slotted cover is typically included to provide electrical insulation of the setscrew. This briefly described complex connection between connectors and leads provides multiple opportunities for malfunction.

Other problematic aspects of conventional pacemakers relate to the separately implanted pulse generator and the pacing leads. By way of another example, the pacing leads, in particular, can become a site of infection and morbidity. Many of the issues associated with conventional pacemakers are resolved by the development of a self-contained and self-sustainable pacemaker, or so-called leadless pacemaker, as described in the applications cited below.

Similar to active fixation implantable leads used with conventional pulse generators, leadless pacemakers are typically fixed to an intracardial implant site by an actively engaging mechanism such as a screw or helical member that screws into the myocardium.

Leadless pacemakers are typically delivered to an intracardial implant site via delivery systems including catheters, sheaths and/or introducers. These delivery systems can be complex and expensive. Also, some such delivery systems can have an associated risk of spontaneous release of the leadless pacemaker from the delivery system, thereby leading to unintended consequences, such as, for example, embolism. Finally, some leadless pacemakers may have an undesirably long overall length for some instances or applications. Accordingly, there is a need in the art for systems and methods that will address these disadvantages.

SUMMARY OF THE DISCLOSURE

Disclosed herein is a system for delivering a leadless pacemaker having a housing with a proximal end. In one embodiment, the system includes a guide catheter. The guide catheter includes a catheter shaft and a negative pressure (e.g., suction) attachment feature. The catheter shaft includes a distal end and a proximal end opposite the distal end. The suction attachment feature is located at the distal end of the catheter shaft and configured to selectively negative pressure adhere (e.g., suction attach) with the housing of the leadless pacemaker.

In one embodiment, the system also includes a source of negative pressure in fluid communication with the suction attachment feature. The source of negative pressure may include a vacuum pump or vacuum chamber attached or attachable with the guide catheter.

In one embodiment, the source of negative pressure may include a negative pressure inducing assembly on, or attachable with, the guide catheter. The negative pressure inducing assembly may include a chamber and a member displaceable within the chamber to change a volume of the chamber. Displacing the member to increase the volume of the chamber results in a negative pressure being communicated to the suction attachment feature. An example of such a negative pressure inducing assembly includes a syringe.

In one embodiment, the suction attachment feature is configured to be mechanically, hydraulically or pneumatically deflected such that deflection of the suction attachment feature modifies its volume. A decrease in volume causes the suction attachment feature to suction adhere to the housing of the leadless pacemaker.

In one embodiment, the suction attachment feature includes a cupule (e.g., suction cup) with a copular (e.g., suction) chamber having a surface contour that is substantially a surface negative of the proximal end of the housing of the leadless pacemaker. The surface contour of the suction chamber may be at least one of semi-spherical, cylindrical, conical, or parabolic.

In one embodiment, the suction attachment feature includes a suction cup with a suction chamber having a shallow concave surface funneling to a suction lumen of the catheter shaft that daylights in the suction chamber at a center of the suction chamber. The relatively shallow concave surface of the suction chamber may pancake or flatten out to adhere via suction to the housing of the pacemaker.

In one embodiment, the suction attachment feature and the housing have similar, but opposite, concave surface contours. When the suction attachment feature suction adheres to the housing, the suction attachment feature goes from having a concave contour to a convex contour to extend along and substantially contact the concave surface contour of the housing.

The suction attachment feature may include a concave flange. The suction attachment feature may be formed of a polymeric material.

In one embodiment, the negative pressure attachment between the negative pressure attachment feature (e.g., cupule, suction cup, etc.) and the housing is sufficient to transfer implantation torque from the catheter shaft to the leadless pacemaker, the transferred implantation torque being sufficient to tissue anchor the leadless pacemaker. In other words the negative pressure attachment between the negative pressure attachment feature and the housing is sufficient that there is no displacement between the negative pressure attachment feature and the housing under implant or explant torqueing of the catheter shaft.

Also disclosed herein is a method for implanting a leadless pacemaker at an implantation site in a patient. In one embodiment, the method includes: negative pressure (e.g., suction) adhering a housing of a leadless pacemaker to an attachment feature at a distal end of a catheter shaft, thereby coupling the catheter shaft to the leadless pacemaker; and upon implantation of the leadless pacemaker at the implantation site, stopping the negative pressure adhering of the housing to the attachment feature to allow the catheter shaft to be decoupled from the leadless pacemaker.

In one embodiment, the method also includes injecting a fluid into the attachment feature as part of the stopping or managing the adhering forces. The adhering can also include receiving a proximal end of the housing into the attachment feature.

In one embodiment, the method is such that the negative pressure attachment between the attachment feature and the housing is sufficient that there is no displacement between the attachment feature and the housing under implant or explant torqueing of the catheter shaft.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 1A and 1B are, respectively, side and end views of an example leadless cardiac pacemaker.

FIG. 3 is an enlarged view of a distal region of FIG. 2 illustrating the leadless pacemaker and the supporting distal end of the delivery system of FIG. 2.

FIG. 4 is an enlarged perspective view of the distal region of the delivery system as viewed from a proximal-side vantage point.

DETAILED DESCRIPTION

Figure 1C:
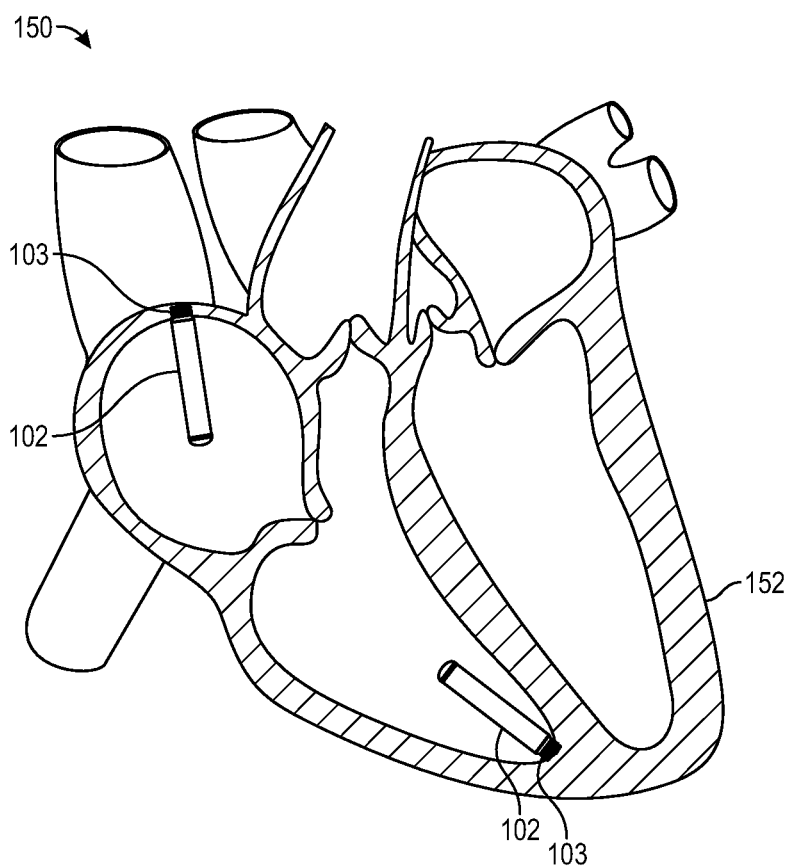
FIG. 1C is a diagrammatic medial-lateral cross section of a patient heart illustrating example implantation of leadless pacemakers in the patient heart.

Disclosed herein is a negative pressure adherence (e.g., suction) equipped catheter delivery system 200 for delivering and implanting leadless pacemakers 102. The system employs a cupule (e.g., suction cup) 216 at a distal end of a catheter of the system for negative pressure (e.g., suction) adhering the distal end of the catheter to a proximal end 156 of a housing 151 of the leadless pacemaker 102.

The system 200 is advantageous for a number of reasons, including reduced manufacturing costs, increased safety (including a decreased risk of spontaneous release of the leadless pacemaker), and increased ease of use. The system 200 is also advantageous in that it allows for the elimination of the tether-based docking features found at the proximal end of leadless pacemakers. Accordingly, leadless pacemakers 102 configured for use with the suction equipped catheter delivery system 200 can have a reduced length and/or provide space for other uses such as, for example, additional electronics, increased battery capacity, etc.

Before beginning a detailed discussion of the delivery system and associated method, a general overview of an example leadless pacemaker 102 and implantation arrangement is provided as follows.

a. Overview of Leadless Pacemaker and Implantation Arrangement

FIGS. 1A-1B illustrate an example leadless cardiac pacemaker 102. The leadless pacemaker 102 can communicate by conducted communication, representing a substantial departure from conventional pacing systems. The leadless pacemaker can perform cardiac pacing that has many of the advantages of conventional cardiac pacemakers while extending performance, functionality, and operating characteristics with one or more of several improvements.

In some embodiments of a cardiac pacing system, cardiac pacing is provided without a pulse generator located in the pectoral region or abdomen, without an electrode-lead separate from the pulse generator, without a communication coil or antenna, and without an additional requirement of battery power for transmitted communication.

FIG. 1C illustrates an embodiment of a cardiac pacing system 150 configured to attain these characteristics. The cardiac pacing system 150 includes one or more leadless cardiac pacemakers 102. Each leadless pacemaker is substantially enclosed in a hermetic housing 151 suitable for placement on or attachment to the inside or outside of a cardiac chamber, such as the right atrium and/or right ventricle of the patient heart 152, as can be understood from FIG. 1B. Attachment of a leadless pacemaker to the cardiac tissue can be accomplished via a helical anchor 103 on an anchor mount 155 extending from a distal end of the leadless pacemaker.

As can be understood from FIGS. 1A-1B, the leadless pacemaker 102 can have two or more electrodes 154, 156 located within, on, or near the housing 151, for delivering pacing pulses to muscle of the cardiac chamber and optionally for sensing electrical activity from the muscle, and for bidirectional communication with at least one other device within or outside the body. The housing can contain a primary battery to provide power for pacing, sensing, and communication, for example bidirectional communication. The housing 151 can optionally contain circuits for sensing cardiac activity from the electrodes 154, 156. The housing contains circuits for receiving information from at least one other device via the electrodes and contains circuits for generating pacing pulses for delivery via the electrodes. The housing can optionally contain circuits for transmitting information to at least one other device via the electrodes and can optionally contain circuits for monitoring device health. The housing contains circuits for controlling these operations in a predetermined manner.

As illustrated in FIG. 1A, the proximal end 157 of the housing 151 may be shaped to facilitate negative pressure (e.g., suction) engagement between the proximal end 157 and a negative pressure (e.g., suction) attachment feature of the delivery system, as described below in detail. In one embodiment, the housing proximal end 157 may be of a smooth surface having a rounded or bull-nosed surface contour, flat or planar surface contour, or other shapes conducive to facilitating a cupule (e.g., suction cup) of the delivery system achieving adequate negative pressure (e.g., suction) attachment to the housing proximal end 157.

In some embodiments, a cardiac pacemaker can be adapted for delivery and implantation into tissue in the human body. In a particular embodiment, a leadless cardiac pacemaker can be adapted for implantation adjacent to heart tissue on the inside or outside wall of a cardiac chamber, using two or more electrodes located on or within the housing of the pacemaker, for pacing the cardiac chamber upon receiving a triggering signal from at least one other device within the body.

Leadless pacemakers or other leadless biostimulators are typically fixed to an intracardial implant site by an actively engaging mechanism or primary fixation mechanism such as a screw or helical member 103 that screws into the myocardium. Examples of such leadless biostimulators are described in the following publications, the disclosures of which are incorporated by reference: (1) US Publication No. US2007/0088394; (2) US Publication No. US2007/0088396; (3) US Publication No. US2007/0088397; (4) US Publication No. US2007/0088398; (5) US Publication No. US2007/0088400A1 on 4/19/2007; (6) US Publication No. US2007/0088405; (7) US Publication No. US2007/0088418; and (8) International Publication No. WO07047681.

In addition to the primary fixation mechanism, such as a helix, some leadless biostimulators may further include a secondary fixation mechanism to provide another feature for keeping the leadless biostimulator in place within the body. Secondary fixation mechanisms can be either active (e.g., the secondary fixation mechanism can actively engage tissue, either within or outside the heart), or can be passive (e.g., the secondary fixation mechanism is not attached to tissue but rather prevents the leadless biostimulator from moving around in the body in the case of accidental detachment). Further details on secondary fixation mechanisms can be found in U.S. application Ser. No. 12/698,969.

Leadless pacemakers or other leadless biostimulators can be delivered to and retrieved from a patient using any of the delivery systems described below. As discussed below in detail, the leadless pacemaker is attached or connected to the delivery system via negative pressure adherence (e.g., suction) and advanced intravenously into the heart. The delivery system includes a cupule with a copular chamber (e.g., suction attachment feature) configured to engage the leadless pacemaker to the distal end of the delivery system to allow the delivery system to be used to deliver the leadless pacemaker to the implantation site and fix the leadless pacemaker to the tissue of the implantation site.

b. Suction Equipped Catheter System for Leadless Pacemaker Implantation

Figure 2:
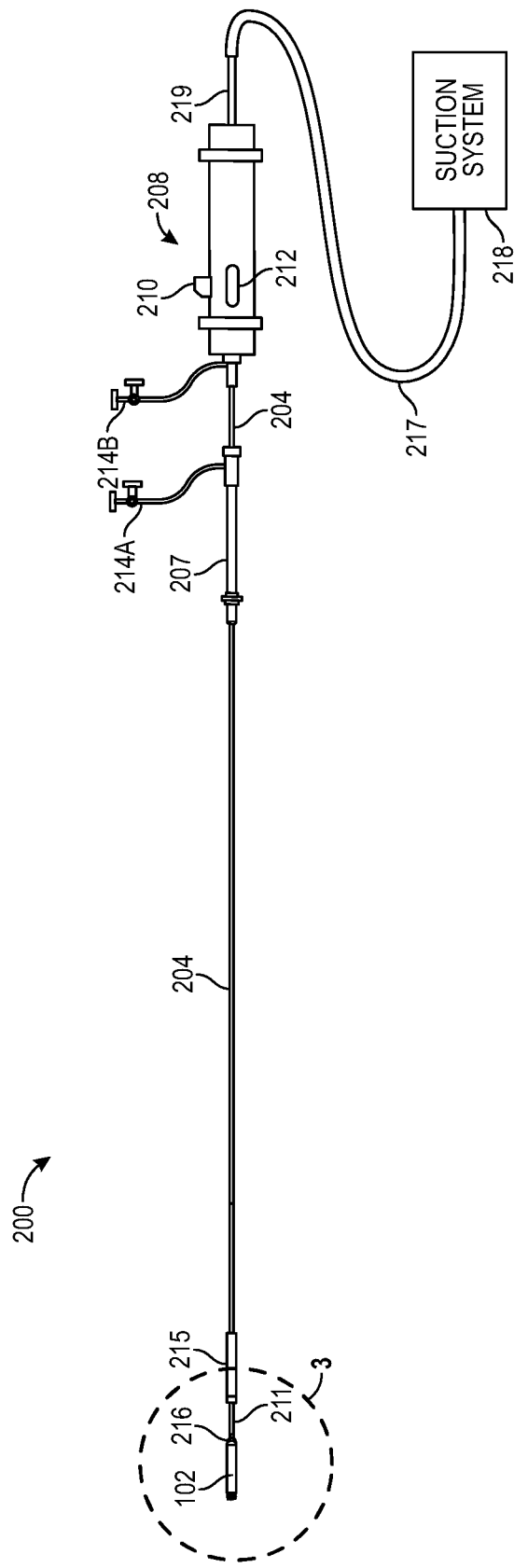
FIG. 2 is a side view of one embodiment of a delivery system for delivering a leadless pacemaker.

FIG. 2 is a side view of one embodiment of a delivery system 200 for delivering a leadless pacemaker 102. As shown in FIG. 2, the pacemaker delivery system 200 includes a delivery sheath 204, guide catheter shaft 211, introducer 207, catheter control handle 208, deflection knob 210, suction control 212, flush ports 214A and 214B, protective sleeve 215, suction line 217, and suction system 218.

The guide catheter includes the handle 208 and of the shaft 211, which extends distally from the distal end of the handle to a distal end of the catheter shaft 211. The distal end of the catheter shaft includes a cupule (e.g., suction attachment feature 216 that suction couples with the proximal end 157 of the leadless pacemaker 102, as described in detail below.

The catheter shaft 211 is both flexible and torqueable. Depending on the embodiment, the catheter shaft 211 may be formed of a polymeric construction and/or metal construction. For example, the catheter shaft 211 may have a traditional catheter lamination construction or have a hollow-helical cable construction.

The deflection knob 210 and suction control 212 are part of the catheter handle 208 at the proximal end of the catheter. The deflection knob may be coupled with deflection members or cables that extend through lumens of the catheter shaft, as known in the art. These deflection members or cables are distally-proximally displaceable relative to the rest of the catheter shaft. Thus, the deflection knob 210 can be used to steer and guide the catheter shaft 211 during implantation and/or removal of the pacemaker.

A suction line 217 extends between the suction system 218 and a proximal end of the handle 208. The suction system 218 is fluidly coupled, via the suction line 217, with a proximal end of a suction lumen 219 (see FIGS. 2 and 3) that extends through the catheter handle 208 and catheter shaft 211 to the suction attachment feature 216. The suction control 212 is configured to allow the user to selectively operate the suction attachment feature 216 between suction "on" and suction "off", thereby allowing the suction attachment feature 216 to adhere via suction to the proximal end 157 of the leadless pacemaker or to decouple therefrom, respectively.

In one embodiment, the suction system may take the form of a vacuum pump or vacuum chamber that provides a source of negative pressure in fluid communication with the suction attachment feature. The vacuum pump or vacuum chamber may be attached or attachable with the guide catheter.

In one embodiment, the suction system may take the form of a source of negative pressure that includes a negative pressure inducing assembly on, or attachable with, the guide catheter. For example, such a negative pressure inducing assembly may include a chamber and a member displaceable within the chamber to change a volume of the chamber. Displacing the member to increase the volume of the chamber results in a negative pressure being communicated to the suction attachment feature). In one embodiment, such a negative pressure inducing assembly may be in form of, or include, a syringe. The syringe, or similar negative pressure inducing assembly, may be fluidly coupled to the catheter, and more specifically, the suction attachment feature 216. Alternatively, the syringe, or similar negative pressure inducing assembly, may be built into the catheter, for example, in the handle of the catheter.

In one embodiment, the negative pressure (e.g., suction) system may take the form of a mechanism by which the cupule (e.g., suction attachment feature) is deflected to change its shape and, as a result, its volume. A decrease in the volume of the suction attachment feature as it is pressed against the housing of the leadless pacemaker causes the suction attachment feature to suction adhere to the housing.

Depending on the embodiment, a mechanical arrangement in the form of a cable, rigid rod, or hydraulic or pneumatic lumen may extend through the catheter shaft from its attachment with the suction attachment feature. Displacement of the mechanical arrangement causes deflection in the suction attachment member such that its suction volume reduces. This reduction results in a negative pressure condition when pressed against the pacemaker housing, thereby causing the suction attachment feature to suction adhere to the housing. Deflection of the cupule (e.g., suction/negative pressure attachment feature) via the mechanical arrangement in an opposite direction will eliminate the negative pressure condition and allow the pacemaker to decouple from the catheter.

The catheter shaft 211 extends through the delivery sheath 204, which extends proximally from the protective sleeve 215 to the proximal flush port 214B. The protective sleeve forms the distal end of the delivery sheath. The delivery sheath 204 extends through the introducer 207, which extends distally from the distal flush port 214A. The catheter shaft 211 is longer than the delivery sheath 204, and the delivery sheath 204 is substantially longer than the introducer 207.

The delivery sheath 204 can be distally-proximally displaced within the introducer 207. The catheter shaft 211 can be distally-proximally displaced within the delivery sheath 204 such that the leadless pacemaker, which is suction attached to the suction attachment feature 216, can be proximally retracted relative to the delivery sheath 204 to reside within the confines of the protective sleeve 215 or distally extended relative to the delivery sheath 204 to be distal the protective sleeve 215, as depicted in FIG. 2. Thus, the delivery sheath 204 can be advanced distally over the catheter shaft 211 to provide additional steering and support for the delivery catheter shaft 211 during implantation and to surround the pacemaker 102 as it is introduced through a trocar or introducer 207 into the patient and negotiated through the patient's vasculature to the implantation site.

The flush ports 214A and 214B can be used to flush saline or other fluids through the shaft of the introducer 207 and the delivery sheath 204, respectively.

FIG. 3 is an enlarged view of the circled distal region of FIG. 2 illustrating the leadless pacemaker and the suction/negative pressure attachment feature 216 suction coupled to the curved or bull-nosed proximal end 165 of the housing 151 of the leadless pacemaker 102 of FIGS. 1A and 1B. FIG. 4 is an isometric view of the same situation illustrated in FIG. 3. As illustrated in FIGS. 3 and 4, the delivery sheath 204 is shown pulled back proximally along the guide catheter shaft 211 to fully expose the pacemaker 102, including its distal helical tissue anchor 103.

Conversely and although not specifically illustrated, it can be understood that the delivery sheath 204 can be extended distally along the guide catheter shaft 211 to fully cover the pacemaker 102 by causing the pacemaker 102 to fully reside within the confines of the protective sleeve 215. Thus, the cardiac tissue is fully protected from the sharp edges of the helix 103 during implantation.

In summary, when the protective sleeve 215 is pulled back proximally, as shown in FIG. 3, the pacemaker 102 is in an exposed, implantation configuration. When the protective sleeve 215 is advanced distally to protect the pacemaker and helix, the pacemaker 102 is in a protected, advancement configuration.

As can be understood from FIGS. 3 and 4, in one embodiment, the cupule (e.g., suction attachment feature) 216 may be in the form of a cupular chamber (e.g., negative pressure cup, vacuum cup or suction cup) 216 that engages the housing proximal end 156 of the leadless pacemaker 102 when a negative pressure (e.g., suction, vacuum, etc.) is administered to the suction cup 216. The negative pressure is generated by the suction system 218 (see FIG. 2) and communicated to the suction cup 216 via the suction lumen 219 of the catheter shaft 211. The suction lumen 219 distally terminates within the confines of the suction cup 216.

As illustrated in FIGS. 3 and 4, the proximal end 156 of the pacemaker housing 151 is docked with the suction cup. Specifically, the proximal end 156 of the pacemaker housing 151 is first received in the confines of the suction cup 216. The suction cup is then adhered to the housing proximal end 156 by placing the suction cup 216 in fluid communication with the suction system 218 via actuating the suction control 212 on the catheter handle 208. With the leadless pacemaker 102 attached in such a suction manner to the suction cup, the delivery of the leadless pacemaker to the implantation site can then take place as follows.

During initial insertion of the delivery system 200 into a patient, a physician can gain access to the patient's venous system with the introducer sheath 207 using the Seldinger technique (not shown). The delivery system 200, including the leadless pacemaker 102, catheter shaft 211, and delivery sheath 204 can then be advanced through the introducer sheath 207 into the patient's venous system to facilitate delivery of the pacemaker 102 into the heart.

After the delivery system 200 is inserted through the introducer sheath 207 into the patient, the protective sleeve 215 can be advanced distally over the leadless pacemaker by causing the delivery sheath 204 to distally displace along the catheter shaft 211. With the protective sleeve 215 isolating the leadless pacemaker 102 and its helical anchor from the surrounding tissue, the leadless pacemaker can be tracked through the patient's venous system to the implantation site in the patient's heart. Upon reaching the implantation site, the protective sleeve 215 can be retracted proximally from about the leadless pacemaker by causing the delivery sheath 204 to proximally displace along the catheter shaft 211. The leadless pacemaker 102, catheter shaft 211 and protective sleeve 215 now appear as depicted in FIGS. 3 and 4.

Figure 5:
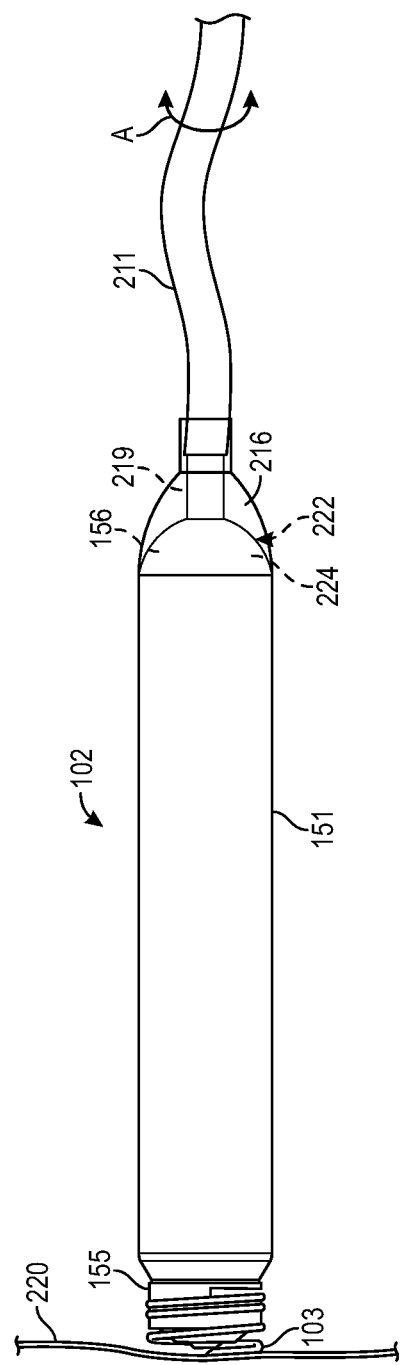
FIG. 5 is the same view as FIG. 3, except depicting the tethered mode whereby the catheter shaft is suction coupled via the suction cup to the pacemaker housing proximal end.

FIG. 5 is the same view as FIG. 3, except depicting the tethered mode whereby the catheter shaft 211 is suction coupled via the suction cup 216 to the pacemaker housing proximal end 156. The tethered mode allows for positioning and repositioning of the leadless pacemaker 102 against a cardiac tissue surface 220. The tethered mode also allows for screwing of the helical anchor 103 into or out of the cardiac tissue to achieve implantation or explantation of the leadless pacemaker, respectively.

As can be understood from FIG. 5, the catheter shaft 211 is flexible so as to deflect as necessary when the pacemaker distal end is forced against the cardiac tissue surface 250. Also, as indicated by arrow A in FIG. 5, the catheter shaft 211 is capable of transmitting torque from the handle to the attached pacemaker 102 to screw the helical anchor 103 into, or out of, the cardiac tissue 220 to result in implantation or explantation of the leadless pacemaker, respectively.

Figure 6:
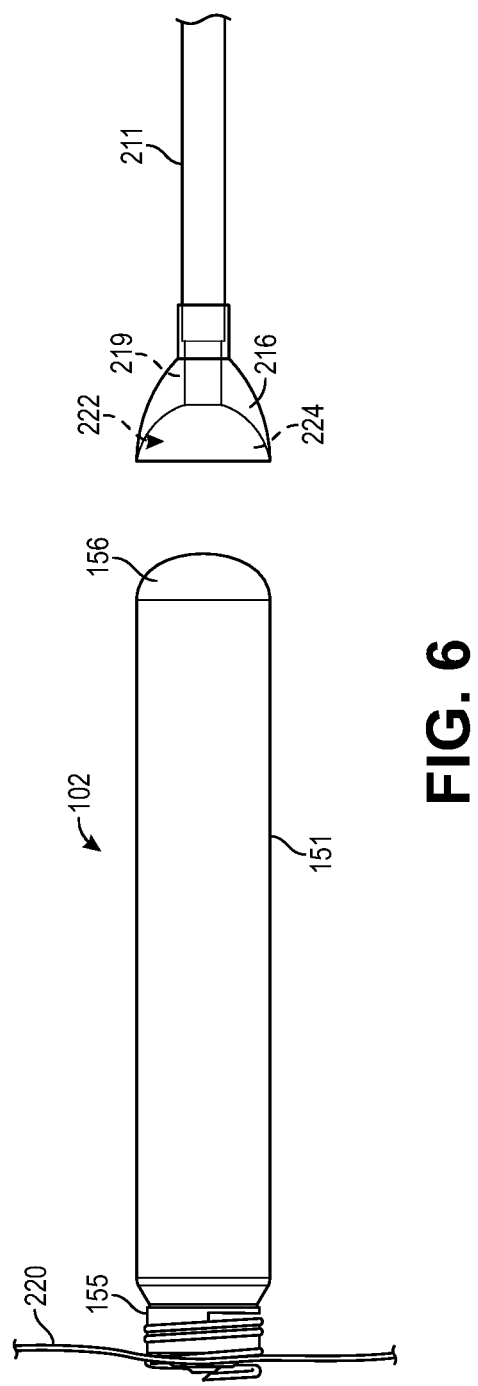
FIG. 6 is the same view as FIG. 5, except illustrating the leadless pacemaker having been released from the suction cup after implantation of the leadless pacemaker in the cardiac tissue of the implantation site.

FIG. 6 is the same view as FIG. 5, except illustrating the leadless pacemaker 102 having been released from the suction cup 216 after implantation of the leadless pacemaker in the cardiac tissue 220 of the implantation site. Specifically, the helical anchor 103 of the implanted leadless pacemaker 102 is now fully imbedded in the cardiac tissue. To achieve the released condition, the negative pressure of the suction system 218 (see FIG. 2) is isolated from the suction cup 216 by actuating the suction control 212 of the catheter handle 208 to suction "off". Alternatively or additionally to shutting off the negative pressure at the suction cup, a puff of saline can be administered through the suction lumen 219 to the suction cup 216 to help push the pacemaker housing proximal end 156 out of the confines of the suction cup 216.

With the implanted leadless pacemaker 102 now decoupled from the delivery system 200, the delivery system can now be withdrawn from the patient, leaving behind the implanted leadless pacemaker, as illustrated in FIG. 6. Advantageously, there would be minimal to no "tug" on cardiac tissue during release of the pacemaker from the suction cup, since in the absence of vacuum, suction, or some form of negative pressure, the pacemaker and the suction cup are not attached to each other. As a result, the catheter is simply allowed to float away from the implanted pacemaker, therefore preventing tissue trauma.

While the implantation of the leadless pacemaker via the delivery system 200 can take place as described immediately above, the process of explantation of an implanted leadless pacemaker can be achieved via the same process in reverse. For example and by way of summary, the suction cup 216 is first moved towards the housing proximal end 156 of the implanted leadless pacemaker 102, as can be understood from FIG. 6. The leadless pacemaker 102 is docked with the suction cup 216 by causing the housing proximal end 156 to be received in the confines of the suction cup, and suction is administered to the suction cup to complete the docking process, as can be understood from FIGS. 3 and 4. Torque is then applied to the catheter shaft 211 to unscrew the helical anchor 103 from the cardiac tissue 220, as can be understood from FIG. 5. The leadless pacemaker 102 can then be covered by the protective sleeve 215 by advancing the delivery sheath 204 distally relative to the catheter shaft 211. With the leadless pacemaker 102 so isolated from the surrounding patient vasculature structures, the delivery system and leadless pacemaker can be withdrawn from the patient.

The above-described suction based leadless pacemaker delivery/retrieval system 200 may employ a variety of suction cup embodiments. For example, the suction cup 216 may have a single geometric profile or a plurality of three dimensional geometric profiles. Regardless of the profile configuration, each suction cup embodiment is shaped in such a way to facilitate adequate suction/negative pressure adherence to the proximal end 156 of the pacemaker housing 151. Correspondingly, the proximal end 156 of the pacemaker housing 151 is shaped in such a way that the suction cup 156 adheres thereto via a vacuum or suction state existing between the proximal end 156 and the suction cup 216. Thus, the suction cup and proximal end of the pacemaker housing are complimentarily configured such that suction adherence of the suction cup 216 to the proximal end 156 is sufficient to maintain the leadless pacemaker attached to the delivery system 200 and allow for adequate torque transmission for implantation or explantation of the leadless pacemaker.

As can be understood from FIG. 6, in one embodiment, the inner confines or suction chamber 222 of the suction cup 216 has a surface contour 224 that is substantially a surface negative of the outer surface of the pacemaker housing proximal end 156, although the size and volume of the suction chamber 222 exceeds that of the housing proximal end 156 to facilitate the proximal end 156 being received in the suction chamber 222. As can be understood from FIG. 5, when the housing proximal end 156 is received in the suction chamber 222, the opposite surfaces 156, 224 generally make continuous mating surface contact. This surface contact is increased upon application of the negative pressure communicated via the suction lumen 219, which daylights in the suction chamber 222 at the center of the suction chamber 222.

In the embodiment depicted in FIG. 6, the opposite surfaces 156, 224 are semi-spherical. However, in other embodiments, the pacemaker housing proximal end 156 may have other shapes (e.g., conical, cylindrical, parabolic, etc.), and the suction chamber 222 and its surface contour 224 will be a surface negative of the shape of the proximal end 156.

Figure 7B:
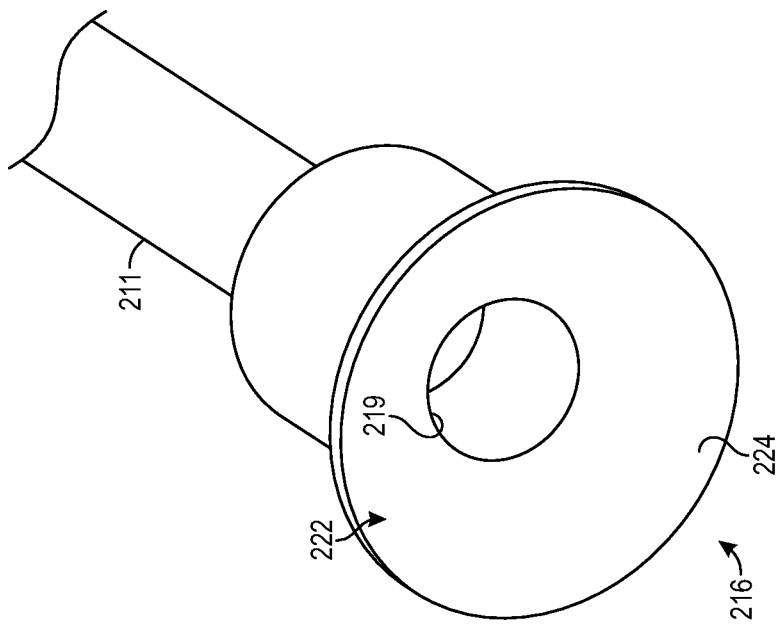
FIGS. 7A and 7B are end isometric views of similar suction cup arrangements.
Figure 7A:
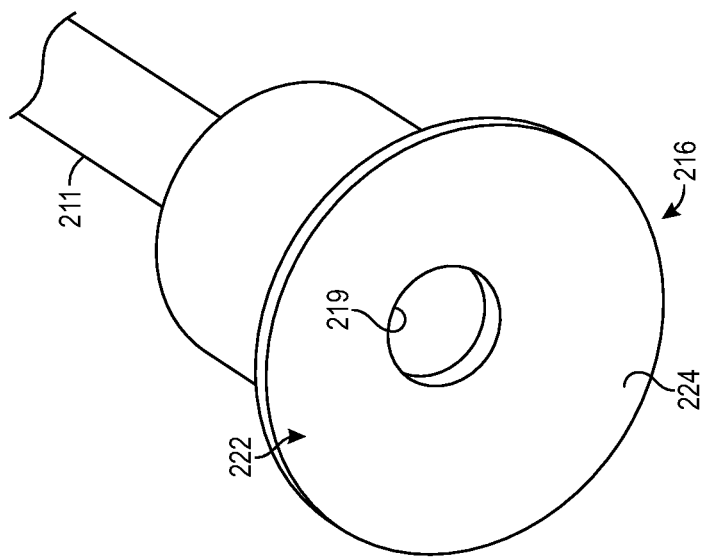
Figure 7C:
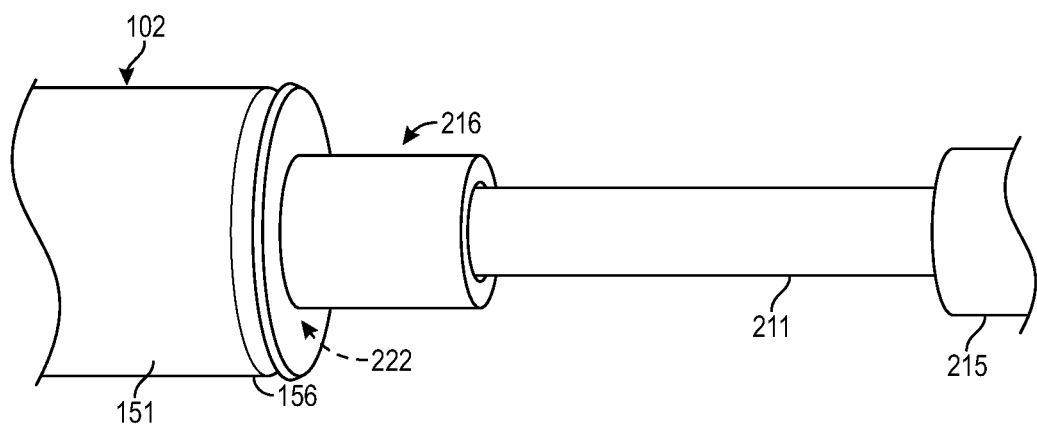
FIG. 7C is a side view of the suction cup similar to those FIGS. 7A and 7B being suction adhered to a proximal end of a leadless pacemaker housing.

In some embodiments as reflected by the suction cups of FIGS. 7A and 7B, the suction chamber 222 is much less spherical than the embodiment of FIG. 6. Instead the suction chamber 222 of FIGS. 7A and 7B may be in the form of a relatively shallow concave surface 224 funneling to the suction lumen 219, which daylights in the suction chamber 222 at the center of the suction chamber. The size of the suction lumen 219 termination in the suction chamber 222 may be smaller, as shown in FIG. 7A, or larger, as depicted in FIG. 7B. In either case, as depicted in FIG. 7C, the pacemaker housing proximal end 156 may be a flat or truncated end of a cylindrical housing shape, and the concave surface 224 of the suction chamber 222 may simply pancake or flatten out to adhere via suction to the flat proximal end 156.

Figure 8A:
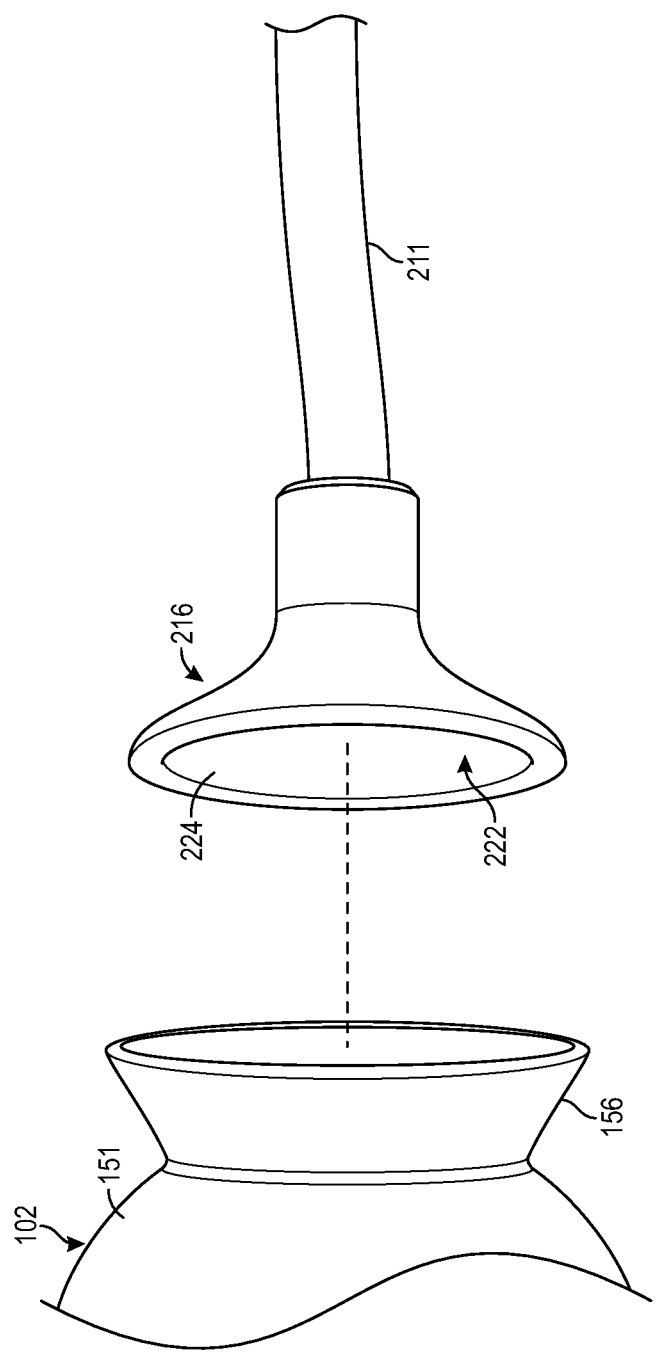
FIG. 8A is a side isometric view of another suction cup arrangement.
Figure 8B:
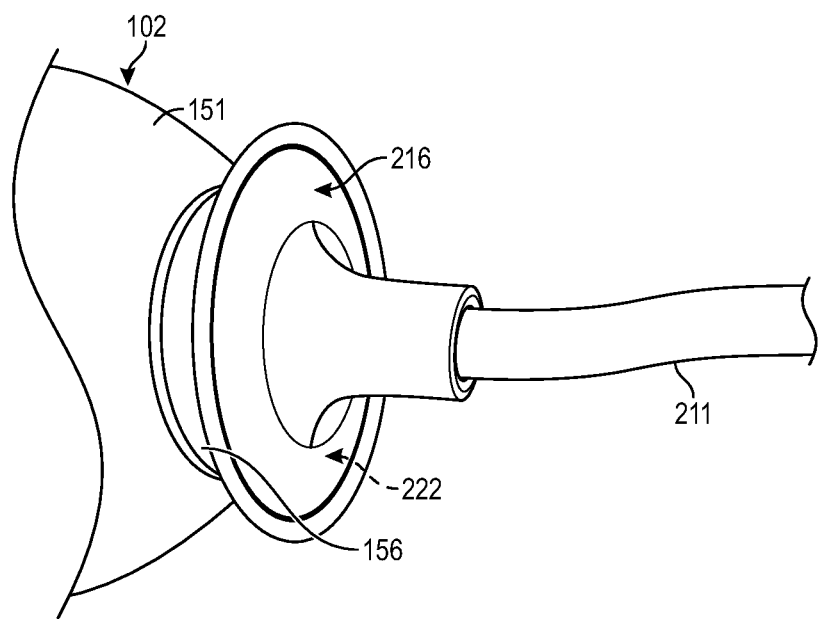
FIG. 8B is a side isometric view of the suction cup of FIG. 8A being suction adhered to a proximal end of a leadless pacemaker housing.

As illustrated in FIG. 8A, the suction chamber 222 may have a concave surface contour 224 that is more spherical than those of FIGS. 7A and 7B and still not be substantially or fully semi-spherical like the embodiment of FIG. 6. As can be understood from FIG. 8A, the housing proximal end 156 is a similar, but opposite, concave surface contour as compared to that of the suction chamber of FIG. 8A. As shown in FIG. 8B, when the suction cup 216 is suction adhered to the housing proximal end 156, the suction cup goes from having a concave contour to a convex contour where the suction cup surface 224 extends along and substantially contacts the concave surface of the housing proximal end 156.

In one version of the embodiment depicted in FIGS. 8A and 8B, the housing proximal end 156 may be a rigid flange having the depicted concave configuration. Alternatively, in another version of the embodiment depicted in FIGS. 8A and 8B, the housing proximal end 156 may be a flexible/compliant flange having the depicted concave configuration, the flexible/compliant flange deforming in a complementary fashion with the suction chamber 222 when the suction cup 216 is suction adhered to the flexible/compliant flange of the housing proximal end 156. In addition to providing strong suction adherence, the flanged proximal end 156 of the embodiment depicted in FIGS. 8A and 8B can provide a feature for retrieval via a delivery/retrieval system employing a snare/grasper arrangement in place of, or in addition to, the suction cup.

Figure 9A:
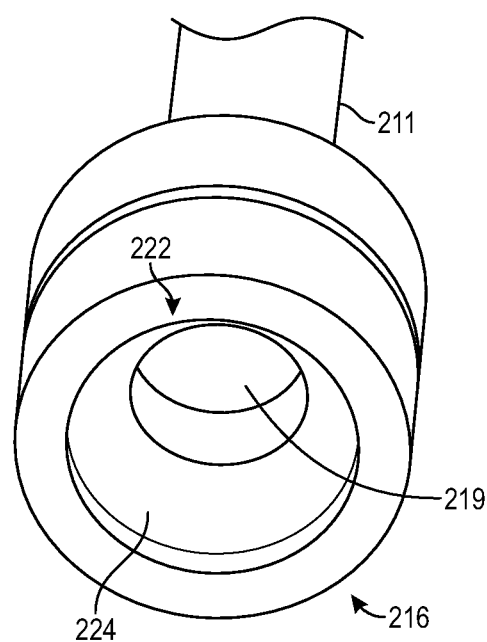
FIG. 9A is an end isometric view of another suction cup arrangement.
Figure 9B:
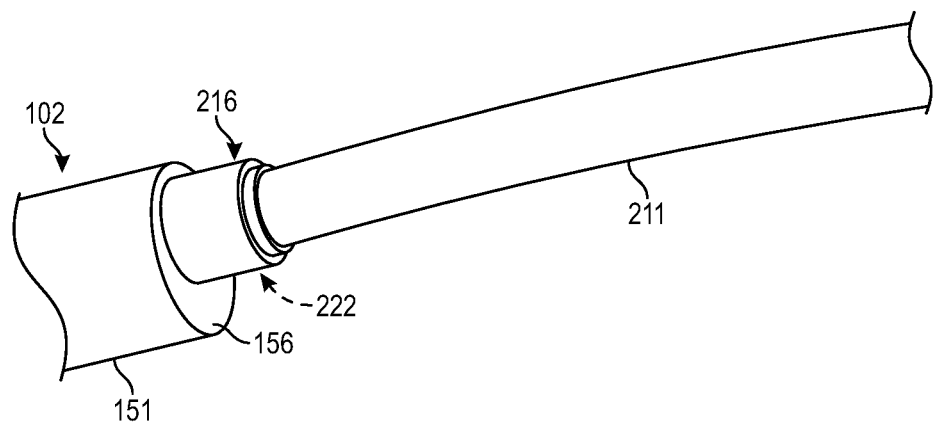
FIG. 9B is a side isometric view of the suction cup of FIG. 9A being suction adhered to a proximal end of a leadless pacemaker housing.

As depicted in FIG. 9A, in some embodiments, the suction cup 216 has a suction chamber 222 that is substantially cylindrical, and the exterior of the suction cup may be similarly cylindrical. As shown in FIG. 9B, such a suction cup 216 does not measurably deflect when suction adhered to a planar proximal end 156 of the pacemaker housing 151.

The suction cup 216 is made of one or more polymeric materials such as, for example, silicone, rubber, polyurethane, silicone rubber-polyurethane-copolymer ("SPC"), or other appropriate biocompatible pliable materials. Depending on the configuration of the suction cup, the suction cup materials may be highly pliable, relatively stiff or something in between.

In summary, the above-described delivery/retrieval system 200 employs a suction based mechanism used for providing torque transmission as well as the coupling between the system 200 and leadless pacemaker 102 in achieving the delivery and implantation of the leadless pacemaker 102 or other type of implant. The suction/negative pressure based mechanism 216 includes a suction cup, vacuum cup, suction flange, or other suction feature that stays attached or grasps onto features of the pacemaker with the help of suction/vacuum applied via internal channels within the delivery catheter. When the suction/vacuum is turned off, the suction cup detaches from the pacemaker, thus detaching the pacemaker from the delivery system. As a result, the delivery system can simply float away from the implanted pacemaker without tugging on the tissue or compression on the catheter.

The system 200 disclosed herein is advantageous for a number of reasons. For example, the system presents a reduced risk of spontaneous or undesired release of an implant from the catheter. The system also provides reliable detachment that is independent of the relative position of the system to the pacemaker.

The system isolates rotation implant forces from the attachment mechanism, thereby eliminating possible binding issues associated with other delivery systems. The system also provides minimal-to-no "tug" on tissue during detachment due to the suction cup simply ceasing to adhere to the pacemaker once the negative pressure is no longer being administered to the suction cup.

The system is easy to use in that it is tool-less and configured for bed-side loading since the suction cup can be attached and detached from the pacemaker simply by turning on and off the suction (respectively). Thus, the system can be used at the bed-side of a patient without exhaustive training, or fixtures. This system feature is very advantageous when multiple implants, such as cardiac pacemakers, need to be implanted inside the anatomy. For example, the system may be used to deliver the first implant/pacemaker. The same system may then be removed from the body, loaded with another implant/pacemaker at the patient's bed-side, and delivered to the implant site as a second implant.

The system offers simple interface mechanisms for delivering torque and facilitating attachment and detachment of a leadless pacemaker. Finally, the system can eliminate the attachment features of the leadless pacemaker that are used with snare or grasping delivery systems, thereby freeing up the real estate of the leadless pacemaker for other uses.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A method, comprising:
adhering a housing of a leadless pacemaker to an attachment feature-of a catheter shaft via a negative pressure between a proximal end of the housing and an opposing surface of the attachment feature, thereby coupling the catheter shaft to the leadless pacemaker; and
further comprising injecting a fluid into the attachment feature as part of managing negative pressure adhering forces between the attachment feature and the housing; and
releasing, upon implantation of the leadless pacemaker at an implantation site, the housing from the attachment feature by stopping the negative pressure, thereby decoupling the catheter shaft from the leadless pacemaker.

2. The method of claim 1 further comprising, receiving, prior to adhering the housing to the attachment feature, the proximal end of the housing into the attachment feature.

3. The method of claim 1, wherein the decoupling of the attachment feature from the leadless pacemaker is atraumatic.

4. The system of claim 1 further comprising applying a torque to the catheter shaft during implantation of the leadless pacemaker at the implantation site, wherein the negative pressure between the attachment feature and the housing is sufficient to transmit the torque from the catheter shaft to the leadless pacemaker.

* * * * *